United States Patent [19]
Mielke et al.

[11] Patent Number: 5,156,954
[45] Date of Patent: Oct. 20, 1992

[54] ASSAY DEVICE AND METHOD USING A SIGNAL-MODULATING COMPOUND

[75] Inventors: Steven T. Mielke, Fremont; Gary E. Hewett, Milpitas, both of Calif.

[73] Assignee: Cholestech Corporation, Hayward, Calif.

[21] Appl. No.: 320,414

[22] Filed: Mar. 8, 1989

[51] Int. Cl.$^5$ .................. C12Q 1/60; C12Q 1/34; C12Q 1/26; C12Q 1/28
[52] U.S. Cl. ........................ 435/18; 435/11; 435/25; 435/28
[58] Field of Search ............ 435/7.71, 7.72, 7.93, 435/11, 18, 19, 20, 21, 25, 28

[56] References Cited

U.S. PATENT DOCUMENTS

| | | | |
|---|---|---|---|
| 3,607,093 | 9/1971 | Stone | 435/25 |
| 3,791,933 | 2/1974 | Moyer et al. | 435/4 |
| 3,907,642 | 9/1975 | Richmond | 435/11 |
| 3,907,645 | 9/1975 | Richmond | 435/11 |
| 3,925,164 | 12/1975 | Beaucamp et al. | 435/11 |
| 3,983,005 | 9/1976 | Goodhue et al. | 435/8 |
| 4,038,485 | 7/1977 | Johnston et al. | 422/55 |
| 4,069,017 | 1/1978 | Wu et al. | 435/4 |
| 4,144,129 | 3/1979 | Gruber et al. | 195/66 |
| 4,144,306 | 3/1979 | Figueras | 422/56 |
| 4,181,575 | 1/1980 | Gruber et al. | 435/11 |
| 4,186,251 | 1/1980 | Tarbutton | 435/11 |
| 4,212,938 | 7/1980 | Gruber et al. | 435/11 |
| 4,234,317 | 11/1980 | Lucas et al. | 436/164 |
| 4,256,693 | 3/1981 | Kondo et al. | 435/25 |
| 4,477,575 | 10/1984 | Vogel et al. | 422/56 |
| 4,503,144 | 3/1985 | Deeg et al. | 435/11 |
| 4,544,630 | 10/1985 | Ziegenhorn et al. | 435/11 |
| 4,654,310 | 3/1987 | Ly | 435/805 |
| 4,680,259 | 7/1987 | Cumbo et al. | 435/11 |
| 4,816,224 | 3/1989 | Vogel et al. | 422/55 |
| 4,820,489 | 4/1989 | Rothe et al. | 422/56 |
| 4,826,421 | 5/1989 | Arai et al. | 435/11 |
| 4,828,983 | 5/1989 | McClune | 435/11 |
| 4,910,134 | 3/1990 | Yamanishi et al. | 435/11 |
| 4,999,289 | 3/1991 | Akiba et al. | 435/188 |

*Primary Examiner*—Douglas W. Robinson
*Assistant Examiner*—T. J. Reardon
*Attorney, Agent, or Firm*—Peter J. Dehlinger

[57] ABSTRACT

An assay device and method for determining the concentration of an analyte. Analyte introduced by liquid absorption into the matrix is used to generate H2O2, via an analyte-specific oxidase, and the $H_2O_2$ is utilized by peroxidase in the presence of peroxidase to convert a substrate reagent to a colored reaction product. A trapping compound in the matrix competes with the substrate reagent, in the presence of the peroxidase enzyme, to produce a silent reaction product, thus proportionately reducing the amount of signal reaction product generated by a given amount of analyte. Detection of a wider range of analyte concentrations is therefore possible.

13 Claims, 4 Drawing Sheets

N-ETHYL-N-SULFOHYDROXY
PROPYL-M-TOLUIDINE (TOOS)

4-AMINO ANTIPYRINE
(4-AAP)

$H_2O_2$

PEROXIDASE

IMINE QUINONE DYE

4-AMINO ANTIPYRINE
(4-AAP)

$H_2O_2$
PEROXIDASE

COLORLESS PRODUCT

ASSAY DEVICE AND METHOD USING A SIGNAL-MODULATING COMPOUND

FIELD OF THE INVENTION

The present invention relates to a method and device for assaying analytes present in a body-fluid sample, and specifically, to an absorptive-pad assay method and device designed for assaying a broad range of analyte concentrations in such a sample.

REFERENCES

Aouidet, A., et al., Clin Chem, 29(11):2001 (1983).
Katterman, R., et al., J Clin Chem Clin Biochem, 22(3):245 (1984).
Kovar, K. A., et al., Clin Chem Acta, 132(3):257 (1983).
Malispina, J. P., et al., Ann Biol Clin, 38(4):207 (1980).
Moshides, J. S., I Clin Chem Clin Biochem, 25(9):583 (1987).
Sharma, A., et al., Clin Biochem, 20(3):167 (1987).

BACKGROUND OF THE INVENTION

Assays for detecting the presence and levels of a variety of analytes in body fluid samples are known. Such assays are often designed for simplicity of use so that they can be reliably conducted in a doctor's office or other clinical setting where personnel may have little training in clinical assay procedure or in interpreting assay results. Typically, such assays involve a one-step assay procedure, or employ automated or semi-automated procedures, with the assay reading being determined from a reaction end-point.

One type of diagnostic assay format which is generally adaptable to a one-step assay protocol is an absorptive-pad device, containing a pad or matrix designed to absorb a sample volume, and to produce an analyte-dependent chemical reaction which can be detected on the pad's surface. Examples of absorptive-pad assay devices and methods are described in U.S. Pat. Nos. 3,983,005, 4,069,017, 4,144,306 and 4,447,575.

In general, it is desirable to carry out a body-fluid assay with an undiluted volume. By avoiding sample-dilution, the number of steps in the assay is reduced, and also the possibility of error in interpreting the assay results is minimized. In the case of a blood sample, using an undiluted sample also minimizes the possibility of blood cell lysis and the effect of variations in blood hematocrit on measured analyte concentration.

One limitation of an absorptive-pad assay format, where an undiluted sample is applied, is that the minimum volume of sample needed to wet the pad may contain an amount of analyte that "saturates" the detection range of the assay. In particular, where analyte detection is based on a color change detected at the surface of the reaction pad, the change in color which is detected, e.g., by reflectance absorptiometry, may be produced at a relative low analyte concentration (in contrast to the same reaction in solution, where changes in the concentration of a colored reaction product can be detected over a wide concentration range). Undiluted sample may therefore contain a higher concentration of analyte than can be effectively quantitated in a absorption-pad device.

An example of this limitation has been encountered in absorptive-pad assays for determination of serum cholesterol. This analyte, which is frequently assayed in a clinical laboratory or doctor's office, is clinically important since high blood cholesterol level, and particularly a high level of cholesterol associated with low-density lipoproteins (LDL), is directly associated with a number of serious disease conditions in humans, including coronary artery diseases, biliary obstruction, and liver or thyroid dysfunctions.

Total cholesterol levels in normal individuals is less than 200 mg/dl, although levels as high as 600–700 mg/dl are present in serious hypercholesteremic conditions. In a typical absorptive-pad assay device, employing for example 5–25 µl serum volumes, color saturation of the pad tends may occur above about 300–350 mg/dl, leaving a significant high-cholesterol range which cannot be accurately quantitated.

U.S. Pat. No. 3,907,645 describes a cholesteral assay method in which cholesterol is used to generate $H_2O_2$ by reaction with cholesterol oxidase, and the $H_2O_2$ is used to generate a visible reaction product by reaction with peroxidase. The patent notes that the amount of colored product produced in the test can be selectively reduced by including increasing amounts of catalase in the assay mixture.

U.S. Pat. No. 4,654,310 proposes the use of a second enzyme or enzyme system to consume analyte or an analyte-produced substrate, to reduce the amount of a reaction product produced by a first enzyme system acting on the analyte. One embodiment of the method employs catalase to compete with peroxidase for consumption of $H_2O_2$ generated by analyte and an analyte oxidase.

One limitation of the catalase quenching method proposed in these patents is that the rate of $H_2O_2$ decomposition by catalase is typically much faster than $H_2O_2$ utilization in product formation. As a result, a catalase concentration which is effective to competitively remove $H_2O_2$ at high $H_2O_2$ concentration (high analyte concentration) will effectively quench the product formation at relatively low $H_2O_2$ concentrations. That is, because the rates of $H_2O_2$-dependent product formation and $H_2O_2$ decomposition by catalase are quite different, the amount of quenching produced by catalase will depend on $H_2O_2$ concentration. The result is either relatively poor sensitivity at low analyte concentration due to excessive $H_2O_2$ decomposition, or relatively little quenching effect at high analyte concentration.

As a further limitation, the relative amount of $H_2O_2$ quenching in the assay system would depend on the relative stabilities of catalase and the analyte-specific enzyme(s) used in the assay.

SUMMARY OF THE INVENTION

It is therefore one general object of the invention to provide a reaction-pad analyte assay method and device which substantially solves or overcomes problems and limitations in the prior art, as discussed above.

It is a more specific object of the invention to provide an analyte assay method and device for determining analyte concentration in a fluid sample, over a broad range of analyte concentrations.

Another specific object is to provide such an assay system and method for use in determination of lipids, including serum cholesterol and triglycerides.

The assay device of the invention includes an absorptive matrix or pad which is effective to absorb a volume of body-fluid sample, and analyte-reaction reagents embedded in the matrix. The reagents include analyte-specific oxidase reagents effective to react with the analyte in the presence of oxygen, with production of $H_2O_2$; a peroxidase enzyme; and a substrate reagent which can be converted to a detectable signal reaction product by the peroxidase enzyme in the presence of $H_2O_2$.

Also embedded in the matrix is a trapping agent effective to compete with the substrate reagent, in the presence of the peroxidase enzyme, to produce a silent reaction product which is distinguishable from the signal reaction product, with utilization of $H_2O_2$. The production of the silent reaction product reduces proportionately the amount of signal reaction product generated by a given amount of analyte. The trapping agent preferably reduces the analyte-dependent amount of signal reaction product formed to between about 10%–70% of the reaction product formed in the absence of trapping agent.

In one preferred embodiment of the invention, the substrate reagent is a binary dye system composed of primary and secondary compounds which are coupled in the presence of $H_2O_2$ and peroxidase to produce a colored signal reaction product. The trapping dye in this embodiment competes with the secondary compound for reaction with the primary substrate to produce the silent reaction product. An exemplary system employs the binary dye system of 4-amino antipyrine and N-ethyl-N-sulfohydroxy propyl-m-toluidine, and a benzenediol trapping compound.

The device may be designed for detection of a variety of analytes, such as total serum cholesterol, serum cholesterol associated with lipoproteins, serum triglycerides, and glucose.

In practicing the method of the invention, a volume of analyte-containing body fluid is applied to the matrix in the device, with absorption of the sample into the matrix initiating the analyte-dependent reaction leading to signal reaction product. The concentration of analyte can be determined either from measured reaction kinetics, or from a measured reaction end point.

These and other objects and features of the invention will become more fully apparent when the following detailed description of the invention is read in conjunction with the accompanying drawings.

DETAILED DESCRIPTION OF THE INVENTION

The assay device of the invention includes an absorptive matrix or pad whose general features are described in Section A. Embedded in the matrix are analyte-reaction reagents which react with analyte in the sample to produce a signal reaction product, via an $H_2O_2$ intermediate, as detailed in Section B. Also embedded in the matrix, according to an important feature of the invention, is a trapping agent which competes with the signal product reaction, with utilization of $H_2O_2$. The nature and mechanism of the trapping agent is considered in Section C, and the assay method, in Section D.

A. Assay Device

Figure 1:
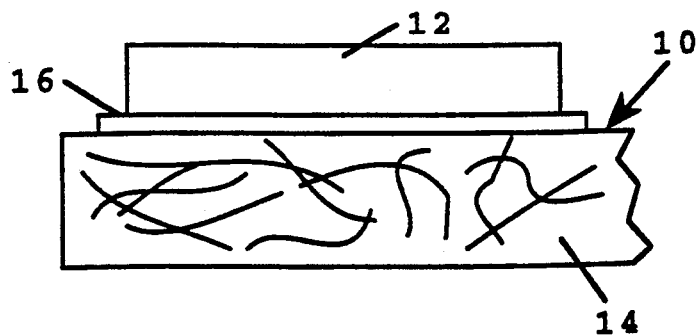
FIG. 1 is a fragmentary side sectional view of an assay device constructed according to the invention.

FIG. 1 shows a fragmentary sectional view of an assay device 10 constructed according to one embodiment of the invention. The device generally includes a reaction pad or matrix 12 and a fluid-delivery strip 14 which is in contact, or contactable, with the reaction pad. A microporous membrane 16 which is carried on the strip separates the strip from the pad during fluid transfer from the strip to the pad.

Pad 12 is an absorbent matrix medium in which the analyte-dependent assay reaction occurs, as will be described below. The pad is preferably formed of a porous fiber or polymer matrix filter material designed to draw aqueous fluid by surface wetting.

A variety of porous materials, such as are used in absorbent filters, including cellulose, cellulose acetate, glass fiber matrices and fused polymer, are suitable materials for the strip and sample pad. The fibers may be crosslinked, if desired, by chemical crosslinking, heat fusion, or the like. Also suitable are porous substrates, such as scintered glass, fused polymer beads, and the like whose wettability and dimension of interstices are such as to promote movement of an aqueous medium into the matrix by surface wetting.

One exemplary pad is a fused polymer porous membrane having dimensions of about 3 mm on a side and about 100–150 $\mu$, and an absorption volume, after complete wetting of the pad of about 0.5–2 $\mu$l.

Strip 14 is preferably formed of a fibrous mesh material designed to draw fluid applied to the strip by surface wetting into and through the strip. That is, a fluid sample applied to one region of the strip will migrate by surface wetting toward opposite the side of the strip. One exemplary strip is a glass fiber filter having a width of 3 mm, a thickness of between about 50–500 microns, and a packing density of between about 0.2 and 0.5 gm/cm$^3$.

In a typical embodiment, a blood fluid sample is applied to the strip either at the opposite (lower) side of the strip or to the right of pad 12 in the figure. As the sample migrates through the strip toward pad 12, the strip's fibrous network retards the movement of particulate matter, including blood cells, acting to partially remove blood cells before the sample reaches pad 12.

Membrane 16 is a microporous membrane designed to filter out blood cells and other particulate matter present in the fluid sample. Where the device is used for assaying total cholesterol or other lipid components which may be associated with large lipoprotein bodies in the blood, the membrane pore sizes are selected to allow passage of these lipid bodies into the reaction pad. One preferred membrane is a polycarbonate membrane available from Nuclepore (Livermore, CA) and having a 1.0 micron pore size.

In the embodiment shown in FIG. 1, the reaction pad 5 is attached to the microporous membrane which is carried on strip 14. Thus, fluid material applied to the strip is carried directly from the strip through membrane 14 into the reaction pad. Alternatively, the pad may normally be positioned in a spaced, i.e., non-contact, position with respect to the strip. Here sample fluid is transferred from the strip to the pad by bringing the pad into contact with membrane 16.

Figure 2:
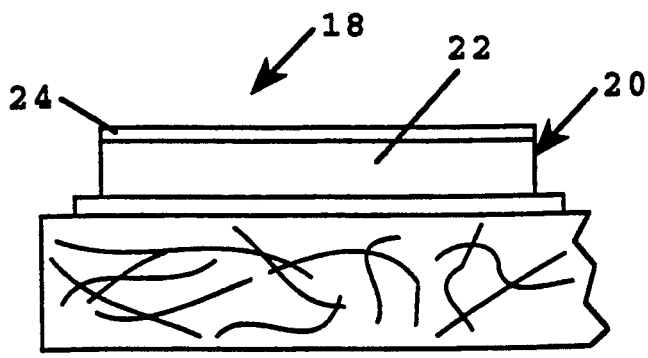
FIG. 2 is a fragmentary side sectional view of an assay device constructed according to another embodiment of the invention.

An assay device 18 constructed according to a second embodiment of the invention is shown in enlarged fragmentary cross-section in FIG. 2. The device differs from device 10 in that the reaction pad, indicated generally at 20, is composed of a lower reagent layer 22 and an upper reference layer 24. The two layers have the same general characteristics as pad 12 described above.

Layer 22 contains reagents for producing a signal reaction product in the presence of reference compound, and layer 24 contains a known amount of a reference compound which when mixed with the reagents in layer 22, with uptake of sample into the pad, produces a quantifiable level of signal reaction product.

The device of the invention is prepared typically by introducing a selected volume of a solution of analyte-reaction reagents (Section B) and trapping agent (Section C) into a dry pad, and dehydrating the pad, such as by lyophilization or evaporation at reduced pressure. Likewise, in a two-layer device, such as device 18, containing a known amount of reference compound in one layer, the two layers are separately prepared with embedded compound(s), then attached to one another, such as by a porous adhesive.

B. Analyte-Reaction Reagents

Figure 3:
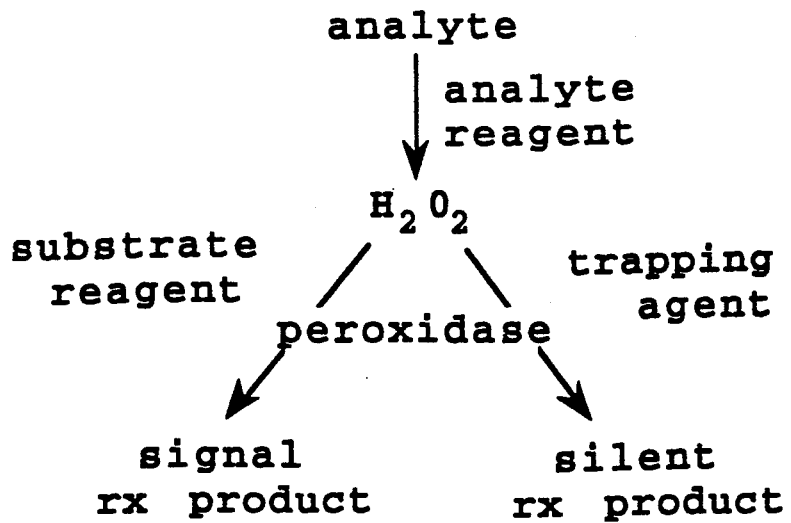
FIG. 3 illustrates general reaction components and products generated according to the method of the invention.

FIG. 3 shows the general components and products formed in the device of the invention, upon absorption of an analyte-containing body sample into the matrix of the device. Generally, as seen, the analyte is converted via an $H_2O_2$ intermediate, to a detectable or signal reaction product. The components in the matrix which carry out the reactions leading to the signal product are referred to collectively as analyte-reaction reagents.

Considering the reaction scheme shown in FIG. 3, initially the analyte reacts with analyte-specific oxidase reagents in the presence of oxygen, with the production of $H_2O_2$. As used herein, the term "analyte-specific oxidase reagents" may include a substrate-specific oxidase which reacts with an analyte or with an enzymatic product of an analyte, and any additional enzymes, cofactors or other reagents needed to convert the analyte to a substrate which can be acted upon by the oxidase enzyme. Alternatively, the oxidase reagents may include a substrate for an analyte $H_2O_2$-generating oxidase. The analyte-specific oxidase reagents are part of the analyte-reaction reagents in the pad.

Table I shows several exemplary analytes for which suitable analyte-specific oxidases exist. As seen, the analytes may themselves be the substrate of the analyte-specific enzyme, as in the case of glucose, uric acid, amino acid oxidase, and free (non-esterified) cholesterol. Here the analyte-specific oxidase reagents may include only the oxidase enzyme.

Alternatively, the analyte may be first converted by primary analyte-specific enzyme(s) to produce the substrate recognized by the oxidase enzyme. Here the analyte-specific oxidase reagents include both the oxidase and additional enzyme for converting the analyte to the oxidase substrate.

In the case of esterified cholesterol, for example, the analyte-specific oxidase reagents include cholesterol esterase, for converting cholesterol in esterified form to free cholesterol, and cholesterol oxidase, which produces cholestenone and $H_2O_2$ in the presence of oxygen.

The analyte-specific oxidase reagents for determination of serum triglyceride include lipase, which hydrolyses triglyceride to glycerol and free fatty acids; glycerol kinase, which converts glycerol to glycerol-phosphate in the presence of ATP; an ATP-generating system; and glycerol-phosphate oxidase, which reacts with glycerol-phosphate to produce dihydroxyacetone-phosphate plus $H_2O_2$.

The analyte-specific oxidase reagents for determination of creatinine include creatinine amidohydrolase, which converts creatinine to urea and sarcosine, and sarcosine oxidase, which converts sarcosine to glycine and formaldehyde, with production of $H_2O_2$.

TABLE I

| Analyte | Substrate | Oxidase |
| --- | --- | --- |
| glucose | glucose | glucose oxidase |
| uric acid | uric acid | uricase |
| amino acid | amino acid | amino acid oxidase |
| free cholesterol | cholesterol | cholesterol oxidase |
| esterified cholesterol | cholesterol | cholesterol oxidase |
| triglyceride | L-glycerol phosphate | L-glycerol phosphate oxidase |
| creatinine | sarcosine | sarcosine oxidase |

It will be appreciated that a variety of other analytes may be assayed by suitable selection of an enzyme or enzyme system capable of reacting with the analyte, with the downstream production of $H_2O_2$ by a suitable substrate-specific oxidase. For example, the analyte may be an enzyme which reacts with a substrate in the analyte-reaction reagents to produce a substrate which can be utilized by, or further reacted for utilization by the analyte-specific oxidase enzyme. Alternatively, the analyte may be an oxidase enzyme capable of reacting with a suitable substrate in the oxidase, where the analyte-specific oxidase reagents now include the oxidase-specific substrate, rather than the oxidase enzyme itself.

With continued reference to FIG. 3, the $H_2O_2$ generated in the analyte-specific oxidase reaction is utilized by a peroxidase enzyme, to convert a substrate reagent to the desired signal product reaction. The peroxidase enzyme is a hydrogen-peroxide oxidoreductase, such as horseradish peroxidase, myeloperoxidase, and lactoperoxidase, which catalyses the reaction:

Donor+$H_2O_2$→oxidized donor+$2H_2O$.

The specificity of the enzyme for the donor is generally low, and a number of phenols, aminophenols, diamines, and indolephenols are active. In the present invention, the donor, or substrate reagent, is selected among a variety of known compounds or pairs of compounds which undergo reaction to a detectable, typically chromogenic reaction product as a result of peroxidase-catalysed oxidation.

Exemplary single donor compounds include O-pheylenediamine, amidopyrine (cited Aovidet reference), and naphthalene-2,3-dicarboxaldehyde (cited Malaspina reference). Typically formation of a colored reaction product involves dimer formation. Examples of donor compound pairs which are suitable include the following primary/secondary compound pairs: 4-aminoantipyrine (4AAP)/2-hydroxy-3,5-dichlorobenzenesulfonate (Sharma), which form a red quinoneimine chromophoric compound with an absorption max at 510 nm; 4AAP/phenol (Ketterman); 4AAP/2,4,6-tribromo-3-hydroxybenzoic acid, which forms quinoneimine dye with an absorption max at 515 nm (Moshides); 4AAP/p-hydroxybenzoate, and 3-methylbenzothiazolin-2-one hydrazone/3-dimethylaminobenzoic acid, which forms a compound with absorption max at 590 nm (Kovar).

For quantitative determination of analyte, it is, of course, important that the level of signal reaction product which is produced be proportional to initial analyte concentration. This requires first, that the amount of $H_2O_2$ available for formation of signal product be dependent on analyte concentration in the reaction mixture, and secondly, that the amount of reaction product generated also be dependent on the amount of $H_2O_2$ formed. These requirements can be met by employing amounts of analyte-specific oxidase reagents, peroxidase, and substrate reagent which are essentially rate limited only by the amount of analyte introduced initially into the reaction pad. Suitable concentrations of the reagents for use in various oxidase-containing assay systems have been reported (see references cited above). The concentrations of the reagents employed in the serum cholesterol assay device described in Examples 1 and in the serum triglyceride assay described in Example 2 are typical.

C. Trapping Agent

As discussed above, one of the limitations of prior art reaction-pad assay systems is the limited range of analyte concentrations which can be assayed, due to color saturation in the pad at relatively low analyte concentrations.

This problem has been solved, according to an important feature of the present invention, by including in the matrix, a trapping agent which is effective to compete with the substrate reagent, in the presence of the peroxidase enzyme, to produce a silent reaction product which is distinguishable from the signal reaction product, with utilization of $H_2O_2$ (FIG. 3). Typically where the signal product has a relatively high absorption coefficient in the visible light range, the silent reaction product is a colorless or weakly colored product.

The trapping agent thus proportionately reduces the amount of signal reaction product generated by a given quantity of analyte, i.e., the level of product which is detected at a given wavelength. Preferably the amount of trapping agent is such as to reduce the amount of signal reaction product formed to between about 10%–70% of the amount formed in the absence of the trapping agent.

Figure 4:
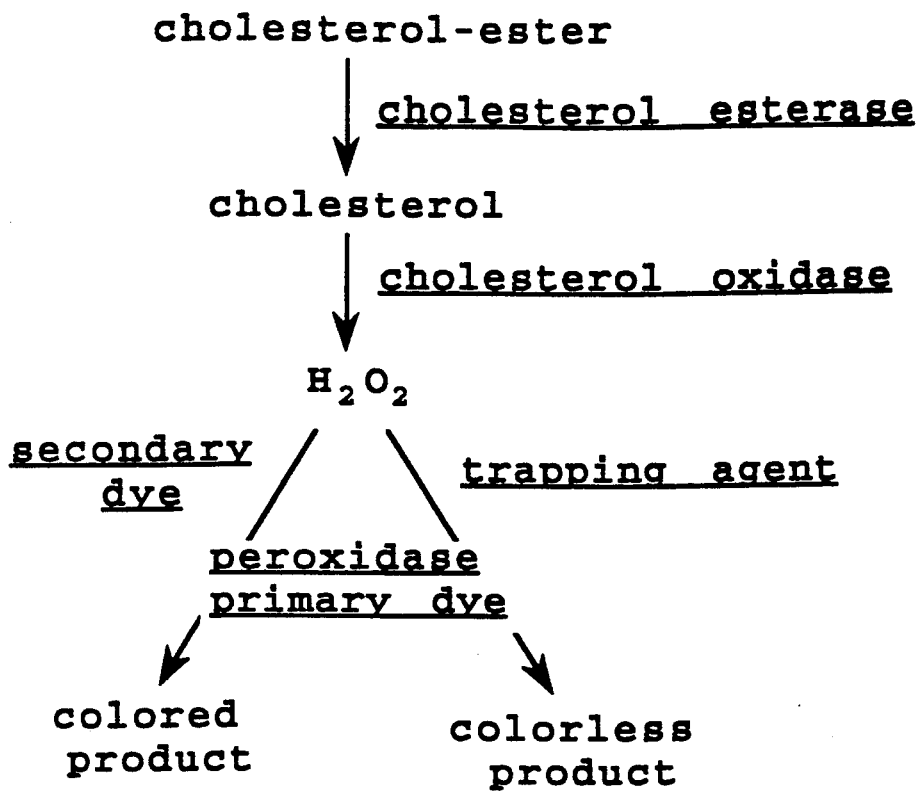
FIG. 4 illustrates the reaction scheme for determination of serum cholesterol in a device like that shown in FIG. 1, where reaction components contained in the devices are indicated by underlining.

The general principles of the trapping reaction are illustrated in FIG. 4, which shows reaction components and products formed in assay devices for detection of serum cholesterol. The reagents embedded in the reaction matrix or pad, are indicated by underlining in the figures.

The analyte-reaction reagents in this scheme include cholesterol ester hydrolase (cholesterol esterase) for releasing esterified cholesterol in free form from serum lipoproteins; cholesterol oxidase, for converting free cholesterol to cholestenone, with the production of the intermediate reaction product $H_2O_2$, a peroxidase; and a substrate reagent consisting of primary and secondary compounds, as described above. The trapping agent also embedded in the matrix is effective to react with the primary substrate in the presence of $H_2O_2$ and peroxidase, to produce a colorless reaction product. Exemplary substrates and trapping agents will be discussed below.

Figure 5:
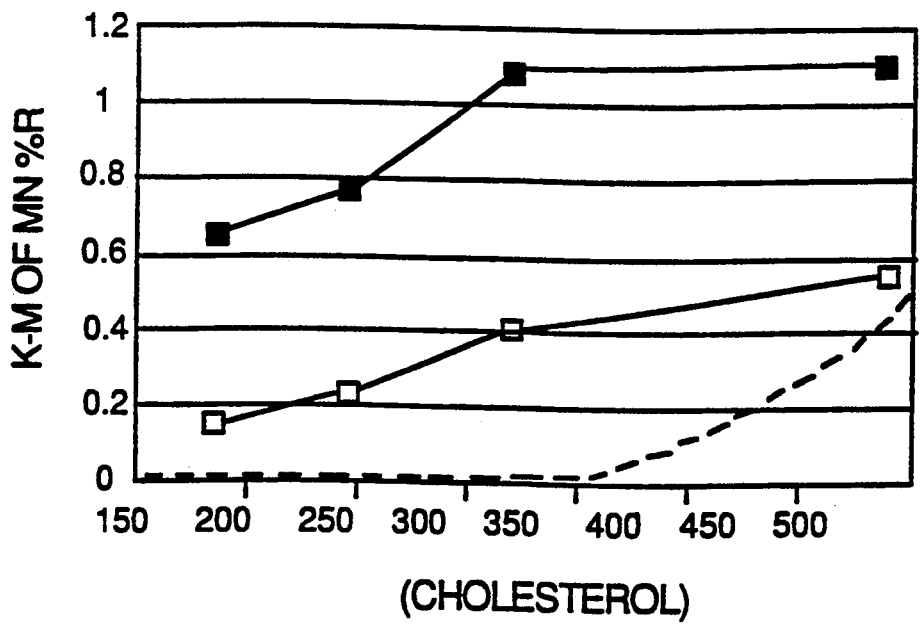
FIG. 5 shows plots of measured reflectance as a function of cholesterol concentration, in the absence (solid rectangles) and presence (open rectangles) of a trapping agent.

The analyte-dependent reduction in signal product in the FIG. 4 reaction scheme is illustrated in FIG. 5, which shows plots of measured signal product formation as a function of serum cholesterol, both with (open rectangles) or without (closed rectangles) trapping agent. As seen in the figure, color saturation (measured by reflectance at 550 nm) occurs at a reflectance value of about 1.1. In the absence of trapping agent, this value is reached with an initial serum cholesterol of between 300–350 mg/dl, which is thus the highest cholesterol concentrations which can be quantitated on the basis of detectable changes in signal product.

In the system containing trapping agent, the amount of signal product produced is at all points proportional to analyte concentration, and generally 60–80% lower than in the absence of trapping agent. The plot demonstrates that a severalfold wider range of cholesterol can be quantitated according to the present invention.

It will be appreciated that the desired analyte-dependent reduction in signal reaction product requires that the consumption of intermediate reaction product in the trapping pathway in fact be competitive with the rate of formation of signal reaction product. If the rate of consumption of intermediate reaction product in the trapping pathway is too slow, little or no reduction in signal product will be observed. On the other hand, if the rate of consumption of intermediate reaction product in the trapping pathway is too rapid, little or no signal product will be produced, at least until the all of the trapping agent is consumed.

An illustration of a system in which the intermediate reaction product is consumed too rapidly by quenching is one in which $H_2O_2$ is rapidly broken down by ascorbic acid used as a quenching agent. Experiments conducted in support of the present invention (Example I) indicate that $H_2O_2$ breakdown is so rapid that essentially no signal product forms until the ascorbic acid is depleted. The theoretical behavior of this system is illustrated by the dashed line in FIG. 5. The formation of signal product here is essentially suppressed up to an analyte concentration at which the quenching agent is depleted by $H_2O_2$. Above this analyte concentration, the reaction curve resembles the upper curve in the figure, where signal product is generated in the absence of trapping agent. Similar results have been observed when catalase is used to quench $H_2O_2$ in a reaction pad.

The limitations of a rapid quenching mechanism then are first that analyte is not detected below a certain threshold level, and secondly, that the range of analyte concentrations which can be detected is still relatively narrow, although shifted toward higher values.

Figure 6:
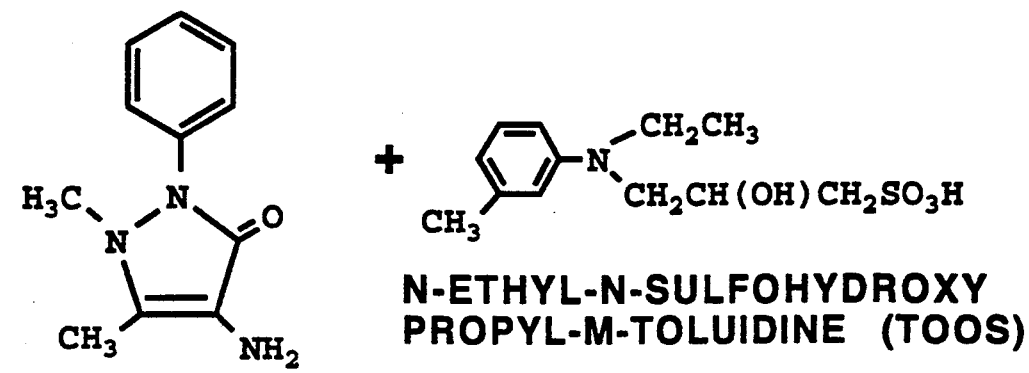
FIG. 6 shows the reaction of two dye components in the presence of $H_2O_2$ and peroxidase to produce a colored reaction product.
Figure 6:
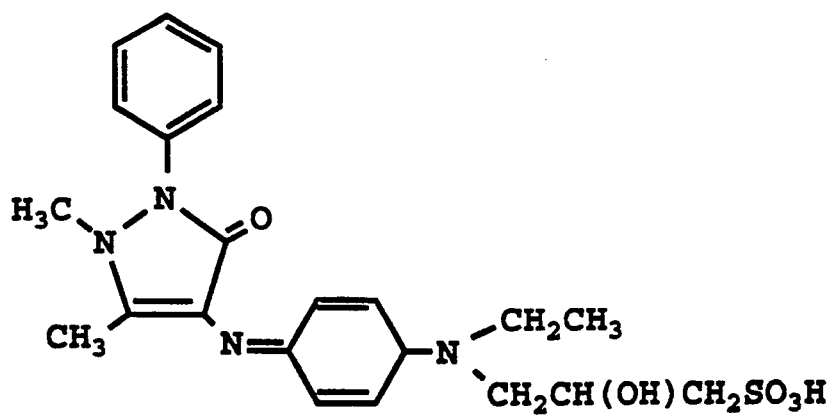
Figure 7:
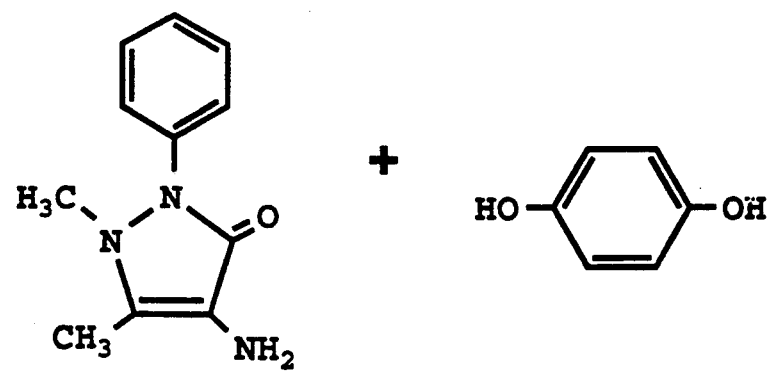
FIG. 7 illustrates a trapping reaction which competes with the FIG. 6 reaction, in the presence of a trapping agent, to produce a colorless reaction product.
Figure 7:
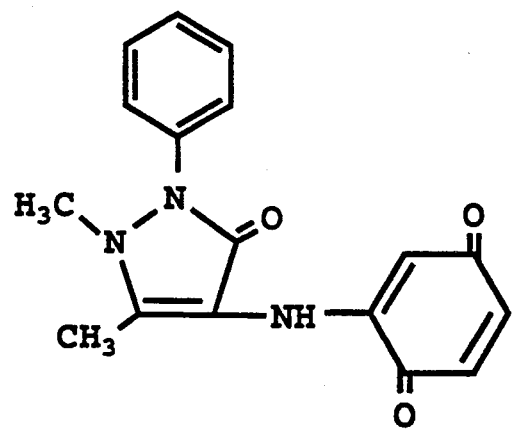

One exemplary reaction system, according to the present invention, is illustrated in FIGS. 6 and 7. The primary substrate here is 4-amino antipyrine (4AAP) and the secondary substrate, N-ethyl-N-sulfohydroxy propyl-m-toluidine (TOOS). The peroxidase-catalyzed reaction, in the presence of $H_2O_2$, produces a purple imine quinone dye having the structure seen at the bottom in FIG. 6. The compound has a strong absorption at about 550 nm.

FIG. 7 shows the reaction produced by a benzenediol trapping dye (1,4,-benzenediol or hydroquinone) in the same reaction system. As seen, the trapping dye here competes with TOOS for reaction with 4AAP, forming an essentially non-chromogenic product shown at the bottom in the figure. The non-chromogenic property of the product is likely due to the ring quinone oxygen groups which are sufficiently electron withdrawing to reduce the double bond character of the ring-carbon/nitrogen bond, such that the resonance structure in the compound necessary for absorption in the visible light range is effectively lost.

Factors which govern the extent to which the trapping dye reduces the amount of signal product formed include the relative concentrations of TOOS and hydroxyquinone, and the relative reactivities of the two compounds with 4APP in the presence of $H_2O_2$ and peroxidase. In one exemplary embodiment, detailed in Example 1, the substrate reagents include 4AAP and TOOS, and the trapping agent is 1,4-benzenediol, at a concentration of about between about 0.5 to 2 mM, and preferably about 1 mM.

Other trapping agents which may be employed in this system include a variety of substituted and benzenediols and related compounds capable of reacting with 4AAP in the presence of $H_2O_2$ and peroxidase, to form a non-colored or weakly colored compound. In particular, compounds capable of reacting with 4AAP or derivatives thereof which have electron withdrawing substituents capable of effectively eliminating resonance between the rings in the product, as indicated above, are suitable. Exemplary agents include 1,3-benezenediol and 1,4,-benezenediol.

Alternatively, in where the two-substrate system above, the trapping agent may compete with the primary substrate for reaction with TOOS, to reduce signal product formation.

In another general embodiment, the substrate reagent is a single compound which typically undergoes peroxidase-catalyzed dimer formation to form a signal reaction product, the trapping agent competes with the dimer reaction, with formation of a silent product formed by coupling the trapping agent to the substrate reagent. Here the trapping agent may be any of a number of substrates which react with the single compound to produce a silent reaction product. As an example, where O-phenylenediamine is employed as a single compound substrate reagent, the trapping agent may be a benezenediol, such as hydroquinone.

D. Assay Method

The present invention also provides a diagnostic method for determining the concentration of an analyte in an aqueous fluid sample, using the assay device described above.

In practicing the method, a fluid sample, and typically a body fluid sample, such as a blood sample, is applied to the absorbent matrix, in an amount which provides a sufficient reaction volume in the pad for accurate determination of signal product. Where the signal product is determined by reflectance from the pad, the applied volume must wet a large enough surface area of the pad to allow accurate reflectance determination from that area.

Ideally, the volume of sample applied to the pad in the device is such as to just wet the entire pad. As noted above, the device is typically designed to wet to completion with 0.5–2 $\mu$l of sample. Where the body fluid being assayed does not contain interfering components, such as red blood cells, or other colored components, the sample may be applied directly to the pad. In the more usual case, the sample is a blood sample which is applied to the fluid-distribution strip which may form part of the device, and which acts to partially remove blood cells in the applied sample. The sample is then filtered through the microporous membrane in the device, to further remove interfering contaminants, and is drawn by contact into the pad in the device.

After addition of the fluid sample to the reactions region(s), the signal value associated with the reaction product is determined. The signal may be determined as a function of time, to determine an analyte concentration based on reaction kinetics. More typically, the signal is measured at or near the reaction end point.

The amount of signal product may be determined visually, by comparison with known color standards, or by reflectance, measuring the intensity of light reflected from the surface of the reaction pad in the device. Other measuring methods, such as pH monitoring, may also be used, where appropriate.

It can be appreciated from the foregoing how various objects and features of the assay device and method are met. The assay device is simple to use, requiring only placement of a single fluid sample on a filter strip. Where the test system is used as part of an automated system, the analyte concentration value can be obtained without additional sample-handling step.

The trapping mechanism of the invention effectively increases the range of detectable analyte concentrations, up to severalfold, while still allowing determination of analyte at low concentrations. Further, the range of detectable analyte concentration can be selectively varied by varying the type and/or concentration of the trapping agent employed. Finally, the trapping mechanism is adaptable to a wide variety of assay formats involving an $H_2O_2$ intermediate reaction product, as described.

EXAMPLE 1

Assay Device for Determining Total Serum Cholesterol

A reaction-intermediate trapping assay system for determining total serum cholesterol was prepared as follows. A 3 mm$^2$, 150 $\mu$ thick porous polymer membrane was infused with 1 $\mu$l of a solution containing 150 U/ml cholesterol ester hydrolase, 10 U/ml cholesterol oxidase, 80 U/ml peroxidase, 20 mM 4-aminoantipyrine (4-AAP), 80 mM reduced N-ethyl-N-sulfohydroxy-propyl-m-toluidine (TOOS), and 1,4,-benzenediol, at a concentration of 1.0 mM. The membrane was dried under reduced pressure. A control pad membrane without trapping agent was also prepared.

The pad was mounted on a solid plastic support by a film adhesive material. A blood fluid sample was applied to a strip of 50 micron thick glass fiber filter (Gelman Sciences, Inc., Ann Arbor, MI), and the sample was allowed to flow laterally in the strip until the red blood cells had been effectively separated from a clear serum fraction migrating through the strip. The pad was then touched to a portion of the strip containing separated serum, to transfer the serum fraction (about 1 $\mu$l) to the pad.

The amount of colored reaction product formed in the reaction pad was determined by reflectance at a wavelength of 550 nm. The amount of signal product measured in the device was compared with that in the control matrix (no trapping agent). The reduction in reflectance was about 92%.

The same reaction was carried out in a second control device containing all of the above reagent components except TOOS. No detectable color reaction was observed, demonstrating that the reaction product between 4AAP and the trapping agent does not produce a colored product.

A similar reaction device employing 1,3,-benzenediol as trapping agent gave a 40% reduction in reflectance. A slight yellow color was observed in a control device containing the same components except lacking the TOOS reagent.

Phenylenediamine was not useful as a trapping agent because its reaction produced an easily detectable yellow/green compound which interfered with detection of signal product.

Dichlorophenols, exemplified by 3,4-dichlorophenol and 2,4,-dichlorophenol, were both ineffective as trapping agents, presumably because of lack of reactivity with 4AAP. No reduction in reflectance in the presence of TOOS, and no colored product in the absence of TOOS were observed.

A similar matrix containing 1 mM ascorbic acid as trapping agent reduced the reflectance by a constant amount, independent of analyte concentration applied to the device.

EXAMPLE 2

Assay Device for Determining Serum Triglycerides

A reaction-intermediate trapping assay system for determining serum triglycerides is prepared as follows. A 3 mm, 150 micron thick fused polymer membrane glass fiber matrix is infused with 1 $\mu$l of a solution containing 400 U/ml lipase, an ATP generating system, 100 U/ml glycerol kinase, 10 U/ml glycerol-phosphate oxidase, 80 U/ml peroxidase, 20 mM 4-aminoantipyrine (4-AAP), 80 mM reduced N-ethyl-N-sulfohydroxy-propyl-m-toluidine (TOOS), and 1,4,-benzenediol, at a concentration of 1.0 mM. The reagent-containing matrix is dried under reduced pressure.

The matrix is mounted on a solid plastic support by a film adhesive material, and the pad is wetted with a serum sample (about 1 $\mu$l) as in Example 1.

The amount of colored reaction product formed in the reaction pad is determined by reflectance at an illuminating wavelength of 550 nm.

Although the invention has been described with reference to exemplary and preferred embodiments and configurations, it will be apparent to those skilled in the art that various changes and modification in reaction components, trapping agents, matrix configuration, and analyte tested can be made without departing from the invention.

It is claimed:

1. An assay test strip for use in assaying the concentration of an analyte in an aqueous fluid sample, where the analyte is one which can serve as a substrate for an oxidase enzyme, with the generation of $H_2O_2$ comprising:
   (a) an absorbent matrix effective to absorb a volume of said sample;
   (b) analyte-reaction reagents embedded in the matrix, including (i) an analyte-specific oxidase enzyme effective to react with analyte present in such a sample to produce $H_2O_2$; (ii) a peroxidase enzyme; (iii) a primary substrate which can be converted from a reduced to an oxidized form by the peroxidase enzyme in the presence of $H_2O_2$, and (iv) a secondary substrate capable of reacting with the oxidized form of the primary substrate to form an analyte-dependent amount of a colored reaction product, and
   (c) a trapping compound embedded in the matrix, which trapping compound is effective to (i) compete with the secondary substrate for reaction with the oxidized form of the primary substrate to produce a substantially colorless product, and (ii) reduce the amount of colored reaction product generated by a given amount of analyte in proportion to the relative amounts of trapping compound and secondary substrate present in the matrix.

2. The test strip of claim 1, wherein the trapping compound is present in the matrix in an amount, relative to the amount of secondary substrate present in the matrix, which is effective to reduce the analyte-dependent amount of said colored reaction product to about 10–70% of the amount of colored reaction product formed in the absence of the trapping compound.

3. The test strip of claim 1, wherein said primary substrate is 4-amino antipyrine, and said trapping compound is a benzenediol.

4. The test strip of claim 3, wherein said secondary substrate is N-ethyl-N-sulfohydroxy propyl-m-toluidine and said trapping compound is selected from the group consisting of 1,3-benzenediol and 1,4-benzenediol, at a concentration of trapping compound substantially in the range between 0.5 mM and 2 mM.

5. The test strip of claim 2, for use in assaying serum cholesterol, wherein said analyte-reaction reagents further include cholesterol esterase, and said oxidase enzyme is cholesterol oxidase.

6. The test strip of claim 2, for use in assaying serum triglycerides, wherein said analyte-reaction reagents includes lipase, a source of ATP, and glycerol kinase, and said oxidase enzyme is glycerol-phosphate oxidase.

7. An assay test strip for use in assaying the concentration of an analyte in a blood sample, where the analyte is one which can serve as a substrate for an oxidase enzyme, with the generation of $H_2O_2$ comprising:
   (a) an absorbent matrix effective to absorb a volume of said sample;
   (b) analyte-reaction reagents embedded in the matrix, including (i) an analyte-specific oxidase enzyme effective to react with analyte present in such a sample to produce $H_2O_2$; (ii) 4-amino antipyrine and a peroxidase effective to oxidize the 4-amino antipyrine inthe presence of $H_2O_2$; and (iii) a secondary substrate effective to react with the oxidized 4-amino antipyrine to produce an analyte-dependent amount of a colored reaction product; and
   (c) embedded in the matrix, a trapping compound which is effective to (i) compete with the secondary substrate for reaction with the oxidized 4-amino antipyrine to produce a substantially colorless product, and (ii) reduce the amount of colored reaction product, generated by a given amount of analyte, in proportion to the relative amounts of trapping compound and secondary substrate present in the matrix, said trapping compound being present in an amount, relative to the amount of secondary substrate in the matrix, which is effective to reduce the analyte-dependent amount of colored reaction product formed to between about 10%–70% of the colored product formed in the absence of trapping compound.

8. The test strip of claim 7, wherein said trapping agent is benzenediol which is effective to react with the oxidized 4-amino antipyrine to produce said non-colored product.

9. The test strip of claim 8, wherein said secondary substrate is N-ethyl-N-sulfohydroxy propyl-m-toluidine and said trapping compound is selected from the group consisting of 1,3-benzenediol and 1,4-benzenediol.

10. A method for assaying the concentration of an analyte in an aqueous fluid sample, where the analyte is one which can serve as a substrate for an oxidase enzyme, with the generation of $H_2O_2$, comprising:
  (a) adding a volume of the fluid sample to an absorptive matrix that contains (i) analyte-reaction reagents, including an analyte-specific oxidase enzyme effective to react with analyte present in such a sample to produce $H_2O_2$, a peroxidase enzyme, a primary substrate which can be converted from a reduced to an oxidized form by the peroxidase enzyme in the presence of $H_2O_2$, and a secondary substrate capable of reacting with the oxidized form of the primary substrate to form an analyte-dependent amount of a colored reaction product; included in the absorptive matrix is a trapping compound which is effective to compete with the secondary substrate for reaction with the oxidized form of the primary substrate, to produce a substantially colorless product, colored reaction product generated by a given amount where the amount of trapping compound includes in the matrix is such as to reduce the analyte-dependent amount of colored reaction product formed:
  (b) by said adding, reacting the analyte with the analyte-specific oxidase enzyme, whereby $H_2O_2$ generated by said reacting is utilized, in the presence of peroxidase, to generate said colored and colorless reaction products, in proportion to the relative concentrations of secondary substrate and trapping compound present in the matrix; and
  (c) determining the amount of colored reaction product formed in the matrix.

11. The method of claim 10, wherein said trapping compound is effective to reduce the analyte-dependent amount of said colored reaction product, as a function of analyte-concentration, to between about 10%–70% of the amount of colored reaction product formed in the absence of trapping compound.

12. The method of claim 10, for use in assaying serum cholesterol, wherein said analyte-reaction reagents further include cholesterol esterase, and said oxidase enzyme is cholesterol oxidase.

13. The method of claim 10, for use in assaying serum triglycerides, wherein said analyte-reaction reagents includes lipase, a source of ATP, and glycerol kinase, and said oxidase enzyme is glycerol-phosphate oxidase.

* * * * *